(12) United States Patent
Landau et al.

(10) Patent No.: US 11,185,267 B2
(45) Date of Patent: Nov. 30, 2021

(54) AUTOMATED SYSTEM FOR MEASUREMENT OF SPATIAL-COGNITIVE ABILITIES

(71) Applicant: THE JOHNS HOPKINS UNIVERSITY, Baltimore, MD (US)

(72) Inventors: Barbara Landau, Baltimore, MD (US); Amy Shelton, Baltimore, MD (US); Gregory D. Hagar, Baltimore, MD (US); Colin Lea, Baltimore, MD (US); Sanjeev Khudanpur, Baltimore, MD (US); Jonathan Jones, Baltimore, MD (US)

(73) Assignee: The Johns Hopkins University, Baltimore, MD (US)

( * ) Notice: Subject to any disclaimer, the term of this patent is extended or adjusted under 35 U.S.C. 154(b) by 415 days.

(21) Appl. No.: 15/784,273

(22) Filed: Oct. 16, 2017

(65) Prior Publication Data

US 2018/0103886 A1    Apr. 19, 2018

Related U.S. Application Data

(60) Provisional application No. 62/409,574, filed on Oct. 18, 2016.

(51) Int. Cl.
| | | |
|---|---|---|
| A61B 5/16 | (2006.01) | |
| A61B 5/00 | (2006.01) | |
| A61B 5/11 | (2006.01) | |
| G09B 1/00 | (2006.01) | |
| G09B 19/00 | (2006.01) | |

(52) U.S. Cl.
CPC ............ *A61B 5/162* (2013.01); *A61B 5/0077* (2013.01); *A61B 5/1113* (2013.01); *A61B 5/4064* (2013.01); *G09B 1/00* (2013.01); *G09B 19/00* (2013.01); *A61B 5/002* (2013.01); *A61B 5/4082* (2013.01); *A61B 5/4088* (2013.01); *A61B 5/4848* (2013.01); *A61B 5/6898* (2013.01)

(58) Field of Classification Search
CPC ..... A61B 5/162; A61B 5/4064; A61B 5/4082; A61B 5/4088; A61B 5/0077; A61B 5/1113; A61B 5/002; A61B 5/4848; A61B 5/6898; G09B 1/00; G09B 19/00
See application file for complete search history.

(56) References Cited

U.S. PATENT DOCUMENTS 7,316,567 B2 * 1/2008 Hsieh ...................... A63H 33/08
                                                    434/171
9,014,614 B2 * 4/2015 Roots ....................... G09B 5/06
                                                    434/362

(Continued)

OTHER PUBLICATIONS

Cheng, et al., Spatial Training Improves Children's Mathematics Ability. Journal of Cognition and Development 2014; 15(1), 2-11.

(Continued)

*Primary Examiner* — Malina D. Blaise
(74) *Attorney, Agent, or Firm* — Johns Hopkins Technology Ventures

(57) ABSTRACT

Described are systems for spatial cognitive ability assessment wherein a subject is able to manipulate one or more object(s) that is monitored by a device for recording motion attached to the object(s), the subject, or both that is able to generate motion electronic data. Also described are methods for assessing spatial cognitive ability.

32 Claims, 5 Drawing Sheets

(56) References Cited

U.S. PATENT DOCUMENTS

| | | | | |
|---|---|---|---|---|
| 9,131,887 | B2* | 9/2015 | Sato | A61B 5/165 |
| 10,195,538 | B2* | 2/2019 | Madsen | A63H 33/042 |
| 10,427,065 | B2* | 10/2019 | Murthy | A63H 33/26 |
| 2002/0192624 | A1* | 12/2002 | Darby | A61B 5/16 |
| | | | | 434/236 |
| 2007/0141541 | A1* | 6/2007 | Chan | G09B 5/06 |
| | | | | 434/236 |
| 2011/0236864 | A1* | 9/2011 | Ashford | A61B 5/4088 |
| | | | | 434/236 |
| 2012/0108909 | A1* | 5/2012 | Slobounov | G16H 50/30 |
| | | | | 600/300 |
| 2012/0189990 | A1* | 7/2012 | Bavelier | G09B 5/06 |
| | | | | 434/188 |
| 2012/0258436 | A1* | 10/2012 | Lee | G09B 19/003 |
| | | | | 434/362 |
| 2013/0266918 | A1* | 10/2013 | Tinjust | A63B 71/0622 |
| | | | | 434/247 |
| 2014/0066802 | A1* | 3/2014 | Kaula | A61B 5/16 |
| | | | | 600/554 |
| 2014/0154651 | A1* | 6/2014 | Stack | G16H 50/30 |
| | | | | 434/236 |
| 2014/0258192 | A1* | 9/2014 | Kim | G16H 20/30 |
| | | | | 706/12 |
| 2014/0303508 | A1* | 10/2014 | Plotnik-Peleg | A61B 5/1117 |
| | | | | 600/483 |
| 2014/0316768 | A1* | 10/2014 | Khandekar | G06F 16/3329 |
| | | | | 704/9 |
| 2014/0323013 | A1* | 10/2014 | Gonzalez-Heydrich | |
| | | | | A61B 5/165 |
| | | | | 446/484 |
| 2015/0125838 | A1* | 5/2015 | Pack | A61B 5/168 |
| | | | | 434/258 |
| 2015/0140529 | A1* | 5/2015 | Tinjust | A63B 69/0053 |
| | | | | 434/236 |
| 2015/0309581 | A1* | 10/2015 | Minnen | G06F 3/017 |
| | | | | 345/156 |
| 2016/0022167 | A1* | 1/2016 | Simon | A61B 5/378 |
| | | | | 600/301 |
| 2016/0029962 | A1* | 2/2016 | Hyde | A63H 3/02 |
| | | | | 600/301 |
| 2016/0262680 | A1* | 9/2016 | Martucci | A61B 5/162 |
| 2017/0112427 | A1* | 4/2017 | Simon | A61B 3/02 |
| 2017/0258390 | A1* | 9/2017 | Howard | A61B 5/16 |
| 2018/0360370 | A1* | 12/2018 | Hamilton, II | A61B 5/4088 |

OTHER PUBLICATIONS

Fennema, et al., The use of spatial visualization in mathematics by girls and boys. J Res Math Edu 1985;16(3), 184-206.

Ferrini-Mundy, Spatial training for calculus students: Sex differences in achievement and in visualization ability. J Res Math Edu 1987;18(2), 126-140.

Hager, et al., Scene parsing using a prior world model. Int J Rob Res 2011;30(2), 1477-1507.

Hegarty, et al., Types of visual-spatial representations and mathematical problem solving. Journal of Educational Psychology 1999;91(4), 684-689.

Hoffman, et al., Spatial breakdown in spatial construction: evidence from eye fixations in children with Williams syndrome. Cogn Psychol. May 2003;46(3):260-301.

Hsi, et al., The role of spatial reasoning in Engineering and the design of spatial instruction. JEE 1997;86(2), 151-158.

Kamii, et al., The development of logico-mathematical knowledge in a block-building activity at ages 1-4. J Res Child Edu 2004;19(1), 44-57.

Lea, et al., An Improved Model for Segmentation and Recognition of Fine-Grained Activities with Application to Surgical Training Tasks. Proc—2015 IEEE Winter Conference on Applications of Computer Vision 2015.

Lea, et al., Learning Convolutional Action Primitives for Fine-grained Action Recognition. IEEE International Conference on Robotics and Automation (ICRA). 2016.

Li, et al., Beyond Spatial Pooling, Fine-Grained Representation Learning in Multiple Domains. Proceedings of 28th IEEE Conference on Computer Vision and Pattern Recognition 2015.

Orion, et al., Relationship between earth-science education and spatial visualization. Journal of Geoscience Education 1997;45, 129-132.

Sorby, Developing 3-D spatial visualization skills. Engineering Design Graphics Journal 1999, 63(2), 21-32.

Stannard, et al., A longitudinal study of the predictive relations among construction play and mathematical achievement. Early Child Development and Care 2001;167(1), 115-125.

Stiles, et al., Cognitive development following early brain injury: Evidence for neural adaptation. TRENDS in Cognitive Sciences 2005;9(3), 136-143.

Tartre, Spatial orientation skill and mathematical problem solving. Journal for Research in Mathematics Education 1990;21(3), 216-229.

Wai, et al., Spatial ability for STEM domains: Aligning over 50 years of cumulative psychological knowledge solidifies its importance. Journal of Educational Psychology 2009;101(4), 817-835.

Wolfgang, et al., Block play performance among preschoolers as a predictor of later school achievement in mathematics. Journal of Research in Childhood Education 2001;15(2), 173-180.

Wolfgang, et al., Advanced constructional play with LEGOs among preschoolers as a predictor of later school achievement in mathematics. Early Child Development and Care 2003;173(5), 467-472.

Casey, et al., The Development of Spatial Skills Through Interventions Involving Block Building Activities. Cognition and Instruction 2008;26(3), 269-309.

Kostopoulos, et al., Children's understanding of large-scale mapping tasks: an analysis of talk, drawings, and gesture. ZDM 2015;47(3), 451-463.

\* cited by examiner

AUTOMATED SYSTEM FOR MEASUREMENT OF SPATIAL-COGNITIVE ABILITIES

REFERENCE TO RELATED APPLICATIONS

This application claims the benefit of U.S. Provisional Patent Application No. 62/409,574, filed on Oct. 18, 2016, which is hereby incorporated by reference for all purposes as if fully set forth herein.

BACKGROUND OF THE INVENTION

Spatial skills—a set of abilities that allows us to mentally represent and transform spatial information in real or imagined space—constitute foundational cognitive tools for learning about and interacting with the world. These skills play an important role in learning and academics (e.g., Cheng & Mix, 2014; Fennema & Tartre, 1985; Ferrini-Mundy, 1987; Hegarty & Kozhevnikov, 1999; Hsi et al., 1997; Kamii et al., 2004; Orion et al., 1997; Sorby, 1999; Tartre, 1990; Wai et al., 2009; Wolfgang et al., 2001; 2003). One of the earliest emerging and widely accessible activities that exercise spatial skills is block play. Although there have been only a few studies attempting to link early block play with later STEM achievement, these have shown that amount of experience with block play (e.g., Legos™) among young children is significantly correlated with later math performance as measured by standardized testing and academic achievement in middle and high school (Stannard et al., 2001; Wolfgang et al., 2001; 2003). Therefore, these early developing spatial skills may be crucial for later academic achievements.

Despite the importance of block-building skills, there has been very limited development of methods to precisely quantify their nature. Although block play is one of the most accessible and ubiquitous activities engaged in by young children, block construction is remarkably complex, tapping into a range of different cognitive skills. Importantly, this complexity is not directly captured in standard techniques of measuring block construction ability; rather, children's block construction is typically quantified by using standardized tests that yield a score capturing overall accuracy. Such tests are available for children ranging from infancy through school age (e.g., Test of Visual Motor Integration, Beery & Beery, 2004; Differential Abilities Scale, Elliott, 1990), and are also part of adult IQ tests (e.g., Wechsler Adult Intelligence Scale; Wechsler, 2008). Developmental norms exist for many of these instruments, providing important diagnostics for children who may have spatial disorders due to brain damage or genetic conditions (Stiles et al., 2005; Landau & Hoffman, 2012). Accurately assessing spatial cognitive abilities potential may enhance the quality of lives including those of children who may be provided specialized training (based on an assessment) enhancing their future success in academics; understanding the effects of drugs given to a person with brain damage by assessing changes to spatial cognitive abilities while on the drug, or by determining the progression of a neurological disease such as Alzheimer based on changes in a patient's spatial cognitive abilities. New systems that accurately assess spatial cognitive abilities must be developed.

SUMMARY OF THE INVENTION

One embodiment of the present invention is a system for spatial cognitive ability assessment including a subject and one or more object(s) comprising an identity, pose, location, color, relative position, orientation, contact points, or combination thereof that is capable of being manipulated by the subject. The system also includes a device for recording motion attached to the one or more object(s), the subject, or both that generates motion electronic data and a device for recording images of the subject, the one or more object(s), or both that generates image electronic data. The electronic device that records images of the subject may include an eye tracking device such as eye tracking glasses that would provide important information about when a person checks between their in-process construction and the model. The system also includes a computer that stores data comprising the motion electronic data, the image electronic data, or a combination thereof, and processes data to assess the spatial cognitive ability of the subject. The device for recording motion and the device for recording images are connected to the computer. In addition, the system includes instructions describing in steps the object manipulation to be performed by the subject. The system data further comprises a time-series of motion electronic data and image electronic data of the object and the subject wherein the computer forms a pattern of manipulation behavior of the subject. Examples of suitable patterns of manipulation behavior include the number of steps taken by the subject to manipulate an object, the number of times a step has been repeated by the subject, the time the subject has taken to complete the steps, the sequence of the subject's steps, or a combination thereof. Patterns of manipulation behavior may further include the identity, pose, location, color, shape, or combination thereof of the one or more object in each of the steps. The system data may further comprise a reference pattern of manipulation behavior; for example, test data of one or more reference subjects tested on the instruments selected from the group consisting of Kaufman Brief Intelligence Test; Differential Ability Scales (DAS), Test of Early Mathematics Ability-3, Mental Rotation, or a combination thereof. One example of reference pattern of manipulation behavior is data on one or more reference subjects administered an agent to treat or prevent a disease such as a neurological disorder, for example, Alzheimer's, a brain injury, or Parkinson's disease. It is suitable for the device for recording motion and the device for recording images to be wirelessly connected to the computer. Suitable objects used in the present invention include blocks and a suitable device for recording motion used in the present invention include an inertial measurement units (IMU). A suitable device for recording images includes a camera, a video recorder, or a combination thereof as examples.

Another embodiment of the present invention is a method for assessing spatial cognitive ability comprising: providing a system for spatial cognitive ability assessment of the present invention; manipulating the one or more object(s) by the subject; processing the data to forming patterns of manipulation behavior; comparing the patterns of manipulation behavior to a reference pattern of manipulation behavior; and assessing the spatial cognitive ability of the subject. A suitable processing step of the present invention includes one or more computer vision technique(s) such as one that automatically identifies the object before and after each manipulation by the subject specifically including the pose, the location, the relative position, the orientation, the contact points or a combination thereof of the objects. In addition, a processing step of the present invention may include one or more blob tracking techniques such as one that identifies the objects, specifically identifies the color, the shape, the location, or a combination thereof of the objects. The methods of the present invention may also include providing a subject instructions describing in steps the object manipulation to be performed by the subject and then having the subject perform the steps. The data obtain from the method of the present invention may include time-series of motion electronic data and image electronic data of the object and the subject performing the steps. The patterns of manipulation behavior comprises the number of steps taken by the subject to complete the step instructions, the number of times a step has been repeated by the subject, time the subject has taken to complete the steps, sequence of the subject's steps, or a combination thereof, and may further include the identity, the pose, the location, the color, the shape, or combination thereof of the one or more object in each of the steps. The reference pattern of manipulation behavior may be obtained from one or more reference subjects each of which have performed the one or more methods of the present invention. The reference pattern of manipulation behavior may be test data of one or more reference subjects tested on the instruments selected from the group consisting of Kaufman Brief Intelligence Test; Differential Ability Scales (DAS), Test of Early Mathematics Ability-3, Mental Rotation, or a combination thereof. The methods of the present invention when assessing the spatial cognitive ability of the subject may demonstrate the subject is normal, has a deficit in spatial cognitive ability, and has an enhancement in spatial cognitive ability (when compared to one or more referenced subjects). The subject may have a disease and the reference pattern of manipulation behavior may be data of one or more reference subjects administered an agent to treat or prevent a disease, such as a neurological disorder who performs one or more methods of the present invention. More specifically Alzheimer's, a brain injury, or Parkinson's disease, as examples. The methods of the present invention may include additional steps such as administering a drug or a behavioral intervention designed to enhance spatial skills to the subject prior, during, or after the subject performs one or more methods of the present invention.

In this disclosure, "comprises," "comprising," "containing" and "having" and the like can have the meaning ascribed to them in U.S. Patent law and can mean "includes," "including," and the like; "consisting essentially of" or "consists essentially" likewise has the meaning ascribed in U.S. Patent law and the term is open-ended, allowing for the presence of more than that which is recited so long as basic or novel characteristics of that which is recited is not changed by the presence of more than that which is recited, but excludes prior art embodiments.

An "inertial measurement unit (IMU)" is defined as an electronic device that measures and reports a body's specific force, angular rate, and sometimes the magnetic field surrounding the body, using a combination of accelerometers and gyroscopes, sometimes also magnetometers.

An "object" is defined as a physical or virtual article such as a physical block or a virtual block observed on a screen, as examples.

A "reference" is defined as a standard or control condition.

A "reference manipulative process" may be generated using the methods of the present invention on a subject without a disease, or without other factors that may impair spatial cognitive ability and sometimes may also include a subject who has an average spatial cognitive ability score.

A "subject" is defined as any human individual or patient to which the method described herein is performed.

DETAILED DESCRIPTION OF THE INVENTION

A system for spatial cognitive ability assessment of the present invention comprises a collection of manipulable objects equipped with video and motion-tracking technology, data processing methods to extract identifiable patterns of manipulation behavior, and data analysis methods that compare the patterns to other groups of individuals or specialized models to compute an assessment of an individual's spatial-cognitive ability. The system for assessing spatial cognitive abilities consists of a data collection component, a raw data analysis component, and an assessment component. An embodiment of these components is described below.

A data collection system using low-cost RGBD cameras (e.g., Microsoft Kinects) and wireless inertial measurement units (IMUs) captures a subject's motions in the block-building task. One or more RGBD cameras are placed above the user's workspace; these are positioned to capture the entire setup to minimize the impact of occlusion. Additionally, one or more wireless IMUs are embedded in the blocks used for the block-building task. Readings from the wireless IMUs and RGBD cameras are recorded and synchronized in time. In some embodiments, IMUs are also attached to the subject's hands, providing an independent measurement of hand motion.

Figure 1:
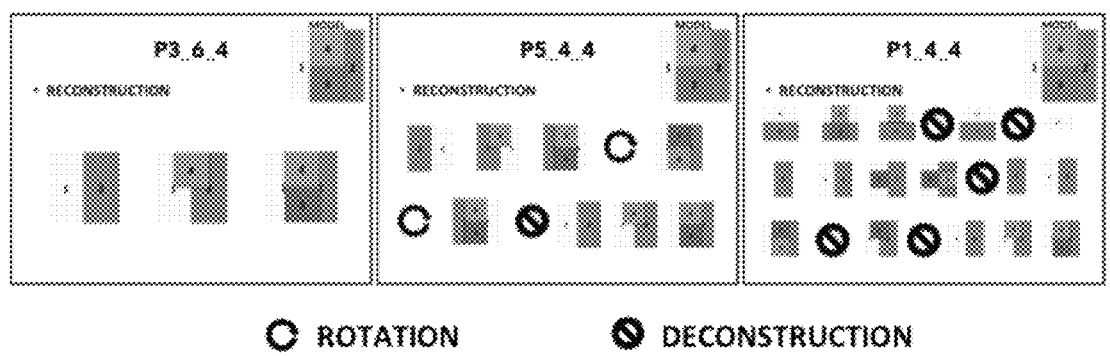
FIG. 1 illustrates a hand-coded reconstruction sequences of the same 4-block model for 3 different participants. Each sequence reflects the movement of the blocks. Numbers are used to identify blocks and do not indicate information about the sequence.
Figure 2:
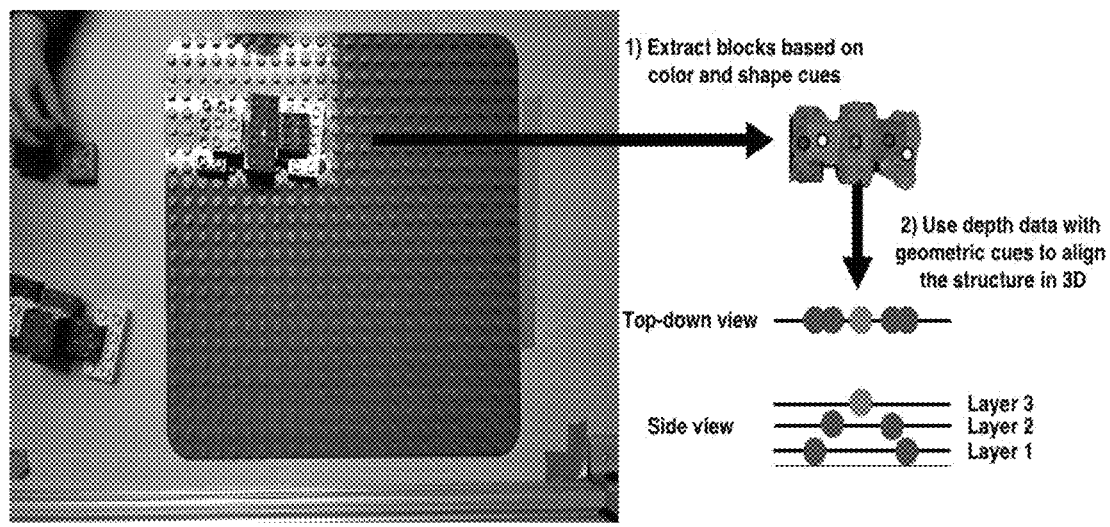
FIG. 2 illustrates an image showing (left) the RGB image and (right) the pixels and corresponding block centroids for each individual object that is part of the structure.

Computer vision techniques automatically extract the identity and pose of each block before and after each manipulative action. The state of the world is then defined by analyzing the spatial relationships (relative position, orientation, and contact points) between each block. Blocks are extracted from color and shape cues using standard blob tracking techniques. The depth data from the RGBD camera can be used to output the 3D configuration of the structure, as depicted in FIG. 2. Manipulative action boundaries are determined by activity in the IMU sensors, video activity, or both. Specifically, initiation and cessation of motion are detected using the IMUs. At each motion cessation, scene analysis is performed to detect changes in the structure being assembled. These changes include both the identity of the block that has been added or removed, and the placement of any blocks that have been added. Fine-grained block pose estimation and scene change analysis can be performed efficiently using sequence scene model editing methods such as those described in Hager and Wegbreit (2011) and Hager et al. (2012). From this segmentation, the inventors will extract a symbolic coding for the actions and effects of each step, similar to that hand coding of FIG. 1. The inventors note that in this process, they will also apply physical constraints to ensure the coding is meaningful. For example, it is not possible to begin manipulation with a red and green block, and create an assembly composed of a blue and yellow block, or to begin with two blocks, but create an assembly consisting of four.

Assessment

Once a sequence of actions and world states (i.e., an assembly sequence) is extracted by the system described above, it is assigned to one or more equivalence classes which characterize the path trajectory. These equivalence classes may be derived in consultation with experts in cognitive science, psychology, and/or early childhood education, or they may arise by the association of a particular pattern of action with a known capability or deficit. The characterization of the equivalence class, in addition to a numerical assessment of proficiency derived from the characterization, is produced as output to the user.

The system described above can be improved by using wireless IMUs to track the motion of one or more of the subject's hands, and one or more cameras that track the subject's gaze. When determining an equivalence class for an observed block construction task, the sequence of actions and world states may be augmented with additional measurements (such as the amount of rotation over time of a block during a placement action).

The system described above can be improved by using a time-series model (such as a Hidden Markov Model or Conditional Random Field) to jointly segment and classify the sequences of video frames and IMU readings when ground truth (hand-annotated) actions are available. Methods for doing so can be implemented based on work such as Lea et al. (2015) and Lea et al. (2016).

The methods for producing assessments may take advantage of the possibility of detecting short sequences, sometimes referred to as action motifs, that are indicative of a particular level of cognitive spatial, or which correlate to a particular category of skill deficit. Methods for detecting such motifs and using them can be found in many available works including Ahmidi et al. (2013).

Applications

The present invention has remarkable potential to translate findings into meaningful changes in practice. There is a greater demand for research aimed at identifying and cultivating individuals to be leaders in STEM-related fields as reports have shown that the United States is falling behind other countries. The connection between spatial skills and performance in STEM activities suggests that any tools developed, such as the present invention, to assess and enhance spatial skills may be important to this effort to improve STEM outcomes. The present invention lends itself naturally to the study of individual differences in spatial skills, which encompasses the characterization of gifted/talented children (many of whom naturally excel in spatial activities) as well as the characterization of children (or adults) with spatial impairments. Spatial and mathematical impairments are often cognitive hallmarks of atypically developing populations, for example, individuals with Williams's syndrome, Down syndrome, and Turner syndrome. Thus, the present invention will naturally provide the characterization and study of a wide range of populations, broadening the implications for education and drug development. Drugs and novel behavioral interventions used to treat these types of disorders may be tested for effectiveness. Patient taking these drugs or participating in novel behavioral interventions will have their spatial cognitive ability assessed at specific time points using the methods of the present invention. The present invention will determine if a drug is capable of enhancing, or decreasing, a patient's spatial cognitive ability over time based on the treatment method employed.

More broadly, the field of education is in need of new tools, such as the present invention, that help teachers to understand the learners in their classrooms at younger ages. In the era of buzzwords like "differentiation" and "personalized learning", the need for ongoing assessment of performance has been widely recognized. A major advantage of the present invention is that it utilizes technology to develop an accessible and scalable assessment. The machine learning insights of the present invention will allow one to refine hand coding and observation in ways that will offer a stronger and more standardized tool. In addition to classroom applications, the present invention is applicable to a wide range of activities requiring some kind of cognitively-guided skilled action. For example, it may be a valuable tool for people involved in activities such as furniture assembly, playing chess, or home construction.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

EXAMPLES

The following Examples have been included to provide guidance to one of ordinary skill in the art for practicing representative embodiments of the presently disclosed subject matter. In light of the present disclosure and the general level of skill in the art, those of skill can appreciate that the following Examples are intended to be exemplary only and that numerous changes, modifications, and alterations can be employed without departing from the scope of the presently disclosed subject matter. The following Examples are offered by way of illustration and not by way of limitation.

Example 1

Measurement of Spatial Cognitive Ability Using Blocks

Children who are "expert" (i.e. highly skilled) builders will sometimes start a construction from the top and other times build the base first, but they get to the end-goal quickly and efficiently, constructing important sub-parts with few moves. By contrast, children who are "novice" (or unskilled) builders may also start at the top or bottom, but they are likely to create more sub-structures and make more placement errors than experts; they also completely take apart their structures once they see an error, rather than simply repairing one or two offending blocks. Although both the expert and the novice may end up with an accurate copy, the steps they take in carrying out the building process are remarkably different, reflecting differences in the sub-units that are constructed, the sequences that lead to global composition, and error-correction. Eleven children (ages 4, 6, and 8 years) complete a series of block constructions. FIG. 1 shows three different children's constructions of the same model. Just from visual inspection, the inventors inferred that the first participant (P3_6_4, age 6) followed a more efficient path than the other two (age 4), quantified as the differences in the number of steps and the number of deconstructions (in which the entire construction is disassembled and the builder starts again). In addition, the inventors saw that P5_4_4 has a construction similar to P3_6_4 but initially establishes the orientation of the base 180° off. The child's rotation of the construction suggests recognition of the problem, which is then corrected by starting over with the base in the correct orientation. P1_4_4 also has orienting difficulties, placing the base at a 90° rotation; however, this participant has much greater difficulty figuring out the necessary correction.

This simple case of three participants completing the same four-block model offers some ideas about how to think more about the process, but even these descriptions are limited by subjective efforts to figure out the patterns. What are the possible patterns and how do novices and experts use them? Are there similarities in patterns across individuals, and/or across different models and more complex models? There are many possible paths to construction forming an enormous class; at the same time, it seems likely that the paths used by experts are quite different from those used by novices. Characterizing those paths that are more typically used by experts vs. novices is not likely to be an easy task, given the extremely large number of possibilities, and the large variation that might be observed even within a particular class of paths. This problem reflects the complexity of the block building process; the solution calls for better tools provided by the present invention.

The present invention comprises a full understanding of this complex process and requires a large data set (to generate as many actual paths as possible) and an accurate way of capturing the moves and their statistical relationships—what move comes first, what move is most efficient after the first, what larger patterns of moves result in the most prominent "chunks", etc. The limits of hand coding (the sole method used in previous research) make it unrealistic to gather large enough quantities of data to capture these complex transitional probabilities and produce a detailed characterization of children's building trajectories over age and expertise.

Example 2

Automated System for Measurement of Spatial-Cognitive Abilities Using Blocks

Participants

Participants will include 120 children aged 4, 6, and 8 years old (40 children at each age). Given that this is uncharted territory, the inventors chose to use these numbers based on a balance between the practicalities associated with testing young children and extensive work on spatial skills and individual differences in the Shelton and Landau labs. These numbers should allow sufficient power (1-≥0.80) to see moderate to large effects within age and small effects across age and over the entire sample. Recruiting will be done through both labs, which have established participant populations from parent listservs as well as local pre-schools and schools.

Procedures

Each child will participate in 2 1-1.5 hour sessions that include the primary block-building task, as well as a short battery of tests and inventories designed to gather data on spatial and math skills as well as children's previous experience with block building.

Block-Building Tasks

For the block-building tasks, children will first be familiarized with the task by completing simple 2-block combinations (which will not be included in the data set). Children will then construct copies of 6 models of increasing complexity, 2 models composed of 4, 6, and 8 blocks each (see FIG. 3). Construction will be time-limited, allowing each child up to 5 minutes to complete his/her construction. All building activity will be videotaped (see below for technology) and children will be instructed to build their copy in a large bounded space on a table directly in front of them. Pilot data from 11 children, ages 4, 6, and 8 years, show that this is easily carried out by young children. In addition, it has already generated interesting observations captured in the step-sequences shown in FIG. 1.

Example Cognitive Tests

After block building, children will be tested on the following instruments: *Kaufman Brief Intelligence Test* (KBIT; *Kaufman & Kaufman,* 1990). This test yields a verbal (receptive vocabulary, verbal reasoning) and nonverbal (conceptual matching) score in addition to an IQ composite score; each of these scores can be correlated with success on the block task. Norms on this test run from 4 years-adulthood. *Differential Ability Scales* (DAS)—*Pattern Construction Subtest* (Elliott, 1990). This test requires children to use colored tiles/patterned cubes to copy 2 and 3D geometric designs. It is normed down to age 3, and will serve as an independent measure of children's block construction ability, which should be highly correlated with success on our block copy task. *Test of Early Mathematics Ability-*3 (*TEMA-*3, Ginsburg & Baroody, 2003). This test measures informal and formal concepts of numbering skills, number-comparison, numeral literacy, mastery of number facts, calculation skills, and understanding of concepts. It will provide a measure of math performance, known to correlate with spatial skills. *Mental Rotation* (adapted from Frick et al., 2003). Because of the high correlation of mental rotation scores with STEM-related achievements (Uttal et al., 2013), we will test children on a simple version of a mental rotation task. The task will be a forced choice "puzzle-like" game where each child will be presented with two rotated stimuli that are mirror images of each other and will need to point to the shape that, when rotated upright, would fit into the hole. Three trials will be presented at each of seven different orientations (from 0° to 180° in steps of 30°) for a total of 21 trials. The correct number of trials will serve as the measure of interest.

Parent survey of their children's play activities: It will be important to know to what extent the child participants have experience in block-building. Children may become proficient builders if, among other things, they simply play with blocks a great deal in informal learning settings. In order to have a measure of children's block play experience, parents will complete a questionnaire designed to assess the frequency of their child's engagement in specific play activities (e.g., plays with blocks, dolls/stuffed animals, reads books, does outside play, watches television, plays video games, puzzles, and board games) and the parents' perceived importance of these same activities; the top three activities for each section will also be identified. Parents will also be asked questions specifically designed to provide a metric for expertise in block play experience (e.g., age the child began playing with blocks, the types of structures typically built and the preferred method of building, etc.). From these items, the inventors will calculate a block experience score from the responses to a subset of questions and a more general spatial score based on frequency of participating in activities that are more spatial in nature (e.g., puzzles).

Characterizing the Microstructure of Block-Play Process

Analysis of the block building will be done in parallel using hand coding and statistical modeling via machine learning techniques. Each type of coding will yield a set of measures that will be analyzed for changes over age group and block model complexity, as first indicators of developmental changes and individual differences. However, the major goal is to characterize individual differences in the solution paths taken by children as they construct block copies. The inventors conceptualize these as differences along the novice/expert continuum. To that end, the first step will be to define each participant as a novice, an expert, or somewhere in between using a comprehensive metric that can serve as the foundation for developing a more fine-grained solution-based metric. In order to capitalize on a combination of measures, the inventors will use the score from the parent survey on block experiences, performance on the DAS Pattern Construction Sub-test, and two general measures from the block building (average number of steps and average time to construct). First, the inventors will examine correlations among these measures to evaluate whether they believe they are measuring related constructs. The inventors expect high correlations if these are all proxies for block-building ability, but the inventors anticipate that they represent some differences as well. All measures will then be z-scored across the entire sample and regularized so that performance associated with expertise (more experience, higher DAS scores, fewer steps, and faster times) is always positive. These will then be summed for each participant to give a composite block expertise score. This composite will serve as the basis for exploring how processes vary as a function of the continuum from novice to expert.

Hand Coding. Hand coding has been the primary method reported in the literature for understanding block building. Even standardized measures such as the Pattern Construction Sub-test from the Differential Abilities Scale suggest that the experimenter indicate the child's final construction by hand coding, as an indication not only of whether it is correct, but what types of gross errors appear (although these do not enter into scoring). Although the inventors have pointed out the limitations of hand coding, the inventors also believe that developing this type of coding can be useful for a) providing more detailed rubrics to other scientists who wish to characterize children's block constructions, and b) aligning it with the results of the statistical modeling approach, with each procedure informing the other. Therefore, the inventors will hand-code at least half of the children's data as follows, generating "maps" representing the sequence of steps a child uses to complete the copy. Each video will be examined to determine the sequence of block placements relative to the front view of the participant—the "step-sequences". Each block will be labeled with a unique number (not visible to the child), and the video will be evaluated frame-by-frame to count all block movements. To be considered a movement, the participant must pick up the block and set it in the bounded building space. Once a block is moved to (or removed from) this space, it will be identified as a step. Steps will be recorded by creating images of each step and creating a slide show of images, representing all steps in a sequence (see FIG. 1). As shown in FIG. 1, a step might also consist of a rotation of the configuration of blocks or subset of the blocks, or a deconstruction (where the child disassembles the structure and starts again). All coded videos will be coded by a primary coder and a secondary coder, and reliability between the two will be established. From the resulting data, the inventors will determine which outcomes are best able to discriminate along the dimension from novice to expert as defined by the composite score.

Step-sequence maps will be analyzed using a variety of measures. Some of these have already been identified, for example, final accuracy, the number of steps to completion of a copy, numbers of rotations and deconstructions during the process. As inventors collect more data, additional measures may emerge, for example, the timing of a rotation within the building process. Pilot data suggest that some children build their copy in a rotated fashion, correctly, and then rotate at the end of the process to orient the copy the same way as the model. Other children may start in one orientation but change the orientation of local parts through the building process, increasing the errors in copying. The orientation from which a child constructs a copy along with his or her reaction to conflicting orientations could be another marker of block-building development. Equally important, the inventors expect that the parallel work on statistical modeling of the block-building data will suggest new ways of thinking of building patterns, which the inventors will then integrate into our hand-coding rubric. All analyses of step-sequences will be carried out over age and block complexity, using standard techniques such as analysis of variance and logistic regression to establish effects of the main factors as well as interactions.

Technology and Statistical Modeling Approach to Coding.

Figure 4:
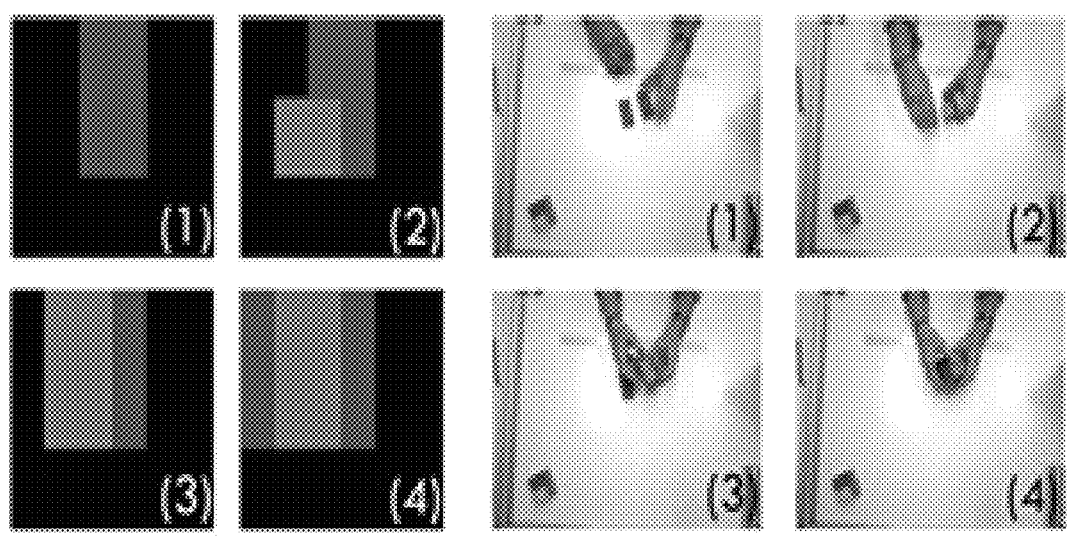
FIG. 4 illustrates examples of a 4-piece block building task: a block graph for each step (left) and the top-down camera view for each (right).

A data collection system using low-cost RGBD cameras (e.g., Microsoft Kinects) has been developed for capturing a subject's motions in the block-building task, and has been used for gathering of pilot data. Similar systems have been developed for analyzing tasks such as toy assembly tasks for human-robot collaboration (e.g., Hawkins et al., 2014). One or more cameras is placed above the user's workspace; these are positioned to capture the entire setup to minimize the impact of occlusion. Analyses are now being developed, as follows. Computer vision techniques similar to those developed by Li, Reiter, and Hager (2015) will be used to automatically extract block identity (through color), its corresponding pose before and after each manipulative action. The state of the world is then defined by analyzing the spatial relationships (relative position, orientation, and contact points) between each block. FIG. 4 depicts the color images taken from the depth camera (right) for a 4-piece structure demonstration as well as the corresponding manually-annotated block graphs (left). The pilot version of this system using a single RGBD camera has already been constructed to confirm the feasibility of this approach. FIG. 4 shows the output of this system. In this pilot, a green placemat is used to differentiate the active workspace from the available pieces. This also aids in aligning the blocks to a common coordinate system. Blocks are extracted using color and shape cues using standard blob tracking techniques. The depth data from the RGBD camera is used to output the 3D configuration of the structure, as depicted in FIG. 4.

The continuous video streams will be automatically segmented into component manipulative actions. This activity will build on our prior work on segmenting surgical videos into component manipulative actions. In particular, the inventors will extend recent work on temporal segmentation using Conditional Random Field models, similar to Lea, Hager, and Vidal (2015), to segment the video into a set of relevant sections (steps) that can be analyzed. From this segmentation, the inventors will extract a symbolic coding for the actions and effects of each step, similar to that hand coding of FIG. 1. The inventors note that in this process, the inventors will also apply physical constraints to ensure the coding is meaningful. For example, it is not possible to begin manipulation with a red and green block, and create an assembly composed of a blue and yellow block, or to begin with two blocks, but create an assembly consisting of four, etc. Further, the inventors will not be analyzing the video sequence as it is acquired, so it will be possible to construct analysis methods that analyze the video data without regard to time or ordering.

Figure 3:
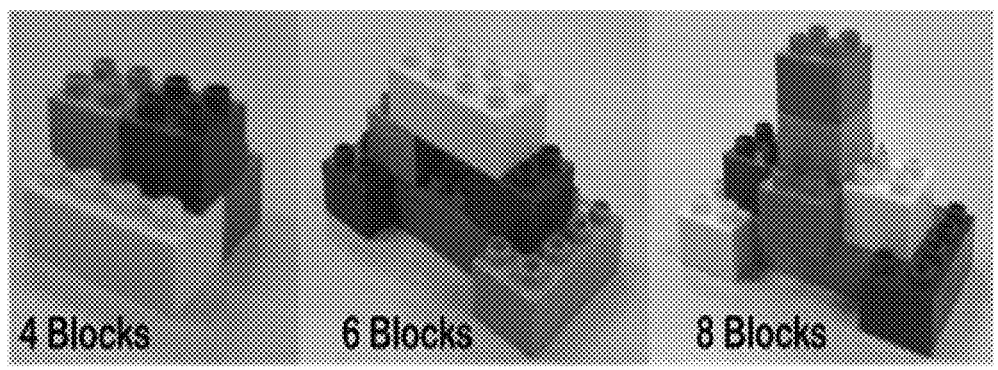
FIG. 3 illustrates examples of 4, 6, and 8 blocks.

Given a corpus of observed data, the objective of the present invention is to discover patterns in the assembly process. The first step will be to further structure the data by representing the assembly of each block structure in terms of a set of motifs, or common subsequences, that appear in multiple trials. In the block-building task an example motif may be taking a long (blue) rectangular block and sequentially adding two (green) square blocks as shown in FIG. 3. Another motif may be joining the two green blocks, and then adding to those blocks the blue blocks. In recent work in the surgical domain, Ahmidi, Hager and colleagues (2013) developed a method for learning these motifs from data using an efficient algorithm for identifying common substrings in a corpus of data. The inventors will identify various levels of abstraction for motif discovery—for example, motifs that involve specific block identities (join two green blocks) vs. motifs that are identity-agnostic (join two blocks of any color). The inventors will also identify various abstractions for representing the construction process in terms of motifs. Much of this investigation of structuring will be done in conjunction with the analysis, described below, to ensure the computational methods are detecting the information relevant for the desired assessments.

The baseline for analysis may include simple metrics such as counting the number of steps a child takes to finish. However, the inventors will identify and use metrics to decipher what cognitive skills actually contribute to being an expert block builder. Given that the present invention is data-driven, the inventors expect that the discovery of motifs will help identify characteristics specific to novice or expert builders. For example, expert-assembled motifs may represent coherent sub-parts of the construction whereas novice motifs may be driven by simple linear adjacency (block x next to block y), without clearly representing parts of the overall structure. The inventors believe that more complicated block structures require specific patterns representing sub-parts that novices are not able to conceptualize. If these patterns can be detected then it may better inform what skills determine how proficient a child is at the task. Additional metrics may be derived from the block graphs. For example, how optimal is the child's assembly? Given a target structure, it is possible to compute all possible ways a child could assembly that structure. Does a user take the "optimal" path according to some metric like time or step-count? If not, how much do they deviate from that path? Can one characterize the set of assembly patterns that a child uses in terms of variability? For example, some of the simplest structures might elicit the very same assembly paths across most children—that is, there may be just a few optimal paths that all children find. At the same time, as structures increase in complexity, it is likely that variation for optimal solutions may also increase; or that the best performers (in terms of time to completion and accuracy) may show a limited number of solutions, while poorer performers show high variability in their solutions. As with the analyses of the hand-coded data, all analyses will be carried out with respect to age group and model complexity. For example, the inventors will plot a histogram representing how many children at each age and for each block model traverse the same paths to solution. The inventors will then evaluate whether the distribution of paths changes over age groups, across experience levels (as determined by parental input forms), etc.

Bringing the Coding Schemes Together

One critical aspect of the present invention is to allow the novel information provided by the machine learning to help define and refine a hand-coding approach. To that end, an iterative approach will take the observations from the machine learning and attempt to apply them to the hand coding. The strength of the relationship between the two types of coding will be established using the most diagnostic measures from each. Next, the participants will be randomly divided into two equal groups, controlling for age. The data from half of the participants will be used to create a rubric for hand coding based on the patterns observed in the machine learning output as measured by a significant improvement in the relationship between one or more of the most diagnostic measures in each coding.

Characterizing the Relationship Between Block-Building and Cognitive, Academic, and Experiential Factors Once the characterization of children's block-building processes and how they may differ over age and model complexity, the present invention will determine how their performance patterns are related to a variety of cognitive, academic, and experiential factors. The two most diagnostic block-building measures from the hand coding and machine learning analyses will be regressed against each of our additional cognitive tests to evaluate different questions of interest. In each case, the simple correlations and beta weights of the regression will provide information about individual block-building measures. Model fits will provide information about block building in general as it relates to these skills.

First, the relationship between block-building measures and DAS pattern construction score will offer the most direct comparison of measures against a more standardized block-building assessment. Next, an assessment of whether block building has a more general relationship to other non-verbal measures by examining the relationship of the block-building measures to mental rotation, an alternative spatial heavily used in individual differences work, and to the KBIT conceptual matching, will be performed to provide a standardized non-verbal measure. The relationship between the block-building measures and the KBIT verbal subscales are expected to be weaker than the three preceding cognitive measures, so the combination of these relationships and their varying degree will offer insights into the domain-specificity of the block-building performance. Finally, the relationship between the block-building measures and scores on the TEMA will provide initial insights into the relevance to academics. One embodiment of the present invention focuses on mathematical skills based on the existing literature, but the overall matrix of relationships may offer ideas about how to think about academic relationships more broadly. The relationships among these factors may vary depending on the use of hand-coded data or the machine-coded block-building measures. The machine-coded data, being more detailed and data-driven than the hand-coded, will improve the predictive value that comes from characterizing block building through either experience or hand-coding. The present invention will reveal more nuanced relationships to other cognitive skills, offering better diagnostics.

Example 3

Interventions to Improve Block-Building

One embodiment of the present invention is to use interventions based on the insights from Example 2 to move children forward along the novice-expert continuum. In essence, take the top 10% of block builders at each age from Example 2, and create a set of instructions based on their most frequent solution paths for each block model, as discovered through the machine-coding data. These instructions will be used to train child participants over a 5-day period, after which the children will be post-tested on their ability to complete the original 6 models plus 3 new models of the same size and complexity of the original ones. The "expert" strategies may be used by non-experts to improve their performance.

Participants

The inventors will test 80 children, including 40 4 year-olds and 40 6 year-olds who have block-building performance at or below the 50th percentile within age group as established by the composite scores in Example 2. The use of the 50th percentile criterion is to avoid having children at ceiling before the training. The focus on our two youngest age groups is based on both concerns about ceiling and the broader goal of targeting interventions to the pre-K and kindergarten age-groups as a first step. Half of the children will be recruited from Example 2, based on their established score. The other half will be recruited separately, and first tested on the Day 1 activities described in Design and Procedure. Those who score below the 50th percentile criterion will be invited back for Days 2-5. Approximately 80 new participants will be run in order to identify 40 non-expert children to achieve the desired sample (20 new children in each age group for a total of 40 per age group).

Design and Procedures

Children will be pre-tested using the same materials as in Example 2. For the half recruited from Example 2, the inventors will confirm their status on the expertise dimension, and for the remaining participants, the inventors will determine whether they qualify to be invited back (hence forming the final sample). Qualified participants will then be randomly assigned to an intervention group or a control group, each of which will participate in a 5-day "block-building mini-camp". Day 1 will be pre-test (60 minutes); Days 2, 3, and 4 will include 30-minute sessions in which children will undergo training or simple "practice", building only one of the two models at each level of complexity. Day 5 will include a post-test, in which the children will again build all 6 pre-test models plus 3 new models, one at each level of complexity.

Figure 5:
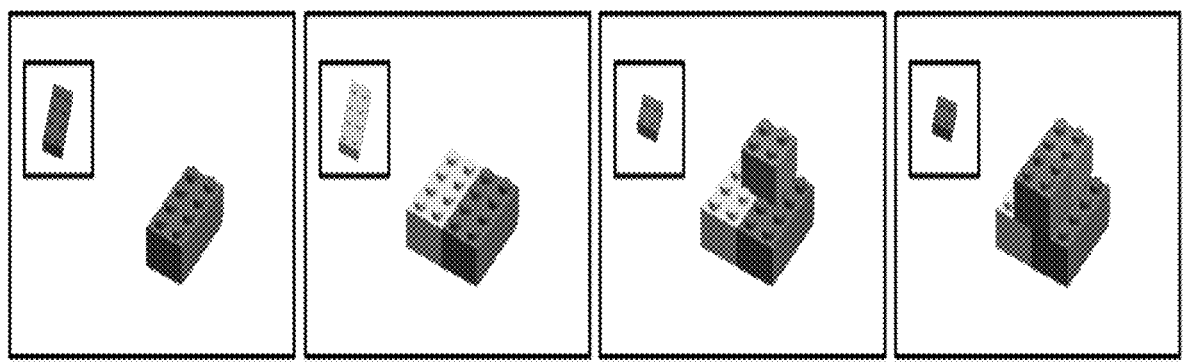
FIG. 5 illustrates a series of instructions based on the expert sequence identified in hand coding the pilot data.

In the Expert Instruction condition, the experimenter will first ask the child to complete each model (run 1) and then show the child a sample instruction page for each model. The instruction page will indicate the "expert" solution using a step-sequence maps derived from the present invention, which will indicate how to move each block to achieve the end result (see FIG. 5). The experimenter will indicate each move to the child as he/she copies the model a second time (run 2) offering encouraging but non-evaluative comments at each step (e.g., Ok; I see). In the control or reference condition, the child will be asked to complete each model twice (run 1, run 2) with no other instruction. The experimenter will sit by the child as in the Expert Intervention, and will again offer the same comments as the child moves each block.

Analyses

The pretest, posttest, and training data on block building will be run through the same procedures as in Example 2 to obtain both summary measures (number of steps, time to copy, etc.) and the detailed characterization of paths. These can then be used to investigate how instructions affect performance during and after practice. The characterization of the block building during the practice with and without expert instructions will provide insights into whether the children can optimize performance while following directions. In this comparison, it is expected that children will follow the instructions in a way that will produce "expert" block-building performance from very early in the practice blocks. That is, as long as they are following the instructions, they will look like experts. By contrast, the children in the control condition may or may not improve over training days, but we do not anticipate seeing expert-like performance early on in the training period.

The critical question is whether the expert instructions or control condition will change the block-building performance between the pre- and post-test. If the expert instructions are effective in teaching children to use more systematic strategies, thus facilitating learning, then the inventors expect expert-like behaviors at posttest in the expert instructions group. However, the inventors also entertain the possibility that instructions will serve as a proxy for learning—a cognitive crutch that allows the child to offload effort. In this case, the inventors would see expert-like behavior during the practice with instructions, but not on the posttest when instructions are again absent, especially for the block construction that was never practiced. The inventors' expectations for the control condition depend, at least in part, on what happens during the training days. If there is any gradual improvement over practice, then it is expected the trajectory to continue into the posttest. In this case, the conditions are not switching from instructions to no-instructions, so any gains during the practice should be maintained or enhanced by the final posttest.

The present invention will provide, for example, appropriate interventions to shape children's block building. Whether the instructions work or not, insights will be provided as to what to try. For example, if instructions prove to be a proxy for learning rather than a facilitator, then an experimenter will want to shift to interventions that guide children to develop the "right" or expert-like solutions. Alternatively, if the expert instructions are sufficiently effective at motivating children to use similar strategies on new models, then an experimenter can pursue them in greater detail to understand what aspects of the instructions are contributing to the effects.

Example 4

Extensions of the Present Invention

The procedures of the present invention may be performed in a virtual world utilizing a computer program, such as an app, on an electronic device such as a computer, iPAD, or cell phone, as examples. The computer program would include all steps of the present invention and would monitor the movement of objects including virtual objects such as electronic blocks viewed on a screen by a subject. Using a touch screen, a subject would be able to select the correct color objects viewed on the screen and move them into their correct positions.

As mentioned, the inventors have already examined the use of computerized block assembly tasks for characterizing the block constructions of typically and atypically developing children, and these studies show close comparability of the results from the virtual task to the real blocks task. An adaptation to the virtual world would create the opportunity to replicate the present invention in this format, and introduce the possibility of scaling up to classrooms in an efficient way.

An example of another possibility would be moving the present invention into a classroom, in order to both offer a replication outside the lab (or controlled environment) and introduce the possibility of scaling up to many classrooms. One embodiment of the present invention (real blocks) may be carried out in schools, introducing teachers to the video set-up of the present invention and arranging for children to carry out the block copy task in a special cubicle fitted with the video equipment. These data would be subject to the same analyses described in the present invention, allowing the replication of findings in a real-world setting, and examine the greater variability among children that could arise from testing in a classroom. The present invention is a powerful approach to characterizing individual differences across the span of spatial talent such as children (or adults) who are spatially impaired due to experiential deprivation (e.g., congenital blindness) or genetic disorder (e.g., Williams syndrome) and has recently begun examining spatial skills in adolescents who have had perinatal strokes. These individuals sometimes exhibit subtle spatial deficits, and the methods of the present invention could serve to characterize these deficits in a more precise way than previously possible. Drugs used to treat these types of disorders may be tested for effectiveness using the methods of the present invention. Patient taking these drugs will routinely have their spatial cognitive ability assessed using the methods of the present invention. The present invention will determine if a drug is capable of enhancing, or decreasing, a patient's spatial cognitive ability over time.

The invention claimed is:

1. A system for spatial cognitive ability assessment of a subject comprising:
   a device for recording motion and images of the subject interacting with an object;
   a sensor configured to measure and transmit data related to motion and position of the object; and
   a processing device configured with processor executable instructions to perform operation comprising:
      receiving data from the device for recording motion and the sensor;
      temporally segmenting the data from the device for recording motion and the sensor into component manipulative actions;
      determining identity and position of the object before and after each one of the component manipulative actions by the subject based on the temporally segmented data from the device for recording motion and the sensor;
      recording the identity and position of the object before and after each one of the component manipulative actions by the subject to create a sequence of actions;
      applying a machine-learning analysis to the sequence of actions to identify patterns in the sequence of actions and determine equivalence classes for the system;
      assigning the sequence of actions to a one of the equivalence classes to assess the spatial cognitive ability of the subject; and
      outputting a characterization of the one of the equivalence classes and a proficiency metric to a display.

2. The system of claim 1, further comprising instructions describing in steps the object manipulation to be performed by the subject.

3. The system of claim 1 wherein the data related to motion and position of the object further comprises a time-series of motion electronic data and the data from the device for recording motion comprises that of the object, the subject, or both wherein the computer forms a pattern of manipulation behavior of the subject.

4. The system of claim 3 wherein the patterns of manipulation behavior comprises a number of steps taken by the subject to manipulate the one or more object(s), a number of times a step has been repeated by the subject, a time the subject has taken to complete the steps, a sequence of the subject's steps, or a combination thereof.

5. The system of claim 4 wherein the patterns of manipulation behavior further comprises the identity, pose, location, color, shape, or combination thereof of the one or more object in each of the steps.

6. The system of claim 3 wherein the data further comprises a reference pattern of manipulation behavior.

7. The system of claim 6 wherein the reference pattern of manipulation behavior is test data of one or more reference subjects tested on the instruments selected from the group consisting of Kaufman Brief Intelligence Test; Differential Ability Scales (DAS), Test of Early Mathematics Ability-3, Mental Rotation, or a combination thereof.

8. The system of claim 6 wherein the reference pattern of manipulation behavior is data on one or more reference subjects administered an agent to treat or prevent a disease.

9. The system of claim 8 wherein the disease is a neurological disorder.

10. The system of claim 9 wherein the neurological disorder is selected from the group comprising Alzheimer's, a brain injury, or Parkinson's disease.

11. The system of claim 1 wherein the device for recording motion and the device for recording images is wirelessly connected to the computer.

12. The system of claim 1 wherein the one or more object(s) are blocks.

13. The system of claim 1 wherein the device for recording motion is an inertial measurement units (IMU).

14. A method for assessing spatial cognitive ability comprising:
 receiving data with a processor from a device for recording motion and images of a subject interacting with an object and receiving data with the processor from a sensor configured to measure and transmit data related to motion and position of the object;
 temporally segmenting the data from the device for recording motion and the sensor into component manipulative actions;
 determining, using the processor, identity and position of the object before and after each one of the component manipulative actions by the subject based on the temporally segmented data from the device for recording motion and the sensor;
 recording, using the processor, the identity and position of the object before and after each one of the component manipulative actions by the subject to create a sequence of actions;
 applying a machine-learning analysis to the sequence of actions to identify patterns in the sequence of actions and determine equivalence classes;
 assigning the sequence of actions to a one of the equivalence classes with the processor to assess the spatial cognitive ability of the subject; and
 outputting, using the processor, a characterization of the one of the equivalence classes and a proficiency metric to a display.

15. The method of claim 14 further comprising using one or more computer vision technique(s).

16. The method of claim 15 wherein the one or more computer vision technique(s) automatically identifies the one or more object(s) before and after each manipulation by the subject.

17. The method of claim 16 wherein the one or more computer vision techniques identities the pose, the location, the relative position, the orientation, the contact points or a combination thereof of the one or more objects.

18. The method of claim 14 further comprising using one or more blob tracking techniques.

19. The method of claim 18 wherein the one or more blob tracking techniques identifies the one or more object(s).

20. The method of claim 19 wherein the blob tracking techniques identifies the color, the shape, the location, or a combination thereof of the one or more objects.

21. The method of claim 14 further comprising providing the subject instructions describing in steps an object manipulation to be performed by the subject, wherein the instructions are provided from the processor to a display on a computing device.

22. The method of claim 14 wherein the sequence of actions comprises a number of steps taken by the subject to complete the step instructions, the number of times a step has been repeated by the subject, time the subject has taken to complete the steps, sequence of the subject's steps, or a combination thereof.

23. The method of claim 22 wherein the patterns of manipulation behavior further comprises the identity, the pose, the location, the color, the shape, or combination thereof of the one or more object in each of the steps.

24. The method of claim 14 wherein the reference pattern of manipulation behavior is obtained from one or more reference subjects each of which have performed the method of claim 14.

25. The method of claim 14 wherein the reference pattern of manipulation behavior is test data of one or more reference subjects tested on the instruments selected from the group consisting of Kaufman Brief Intelligence Test; Differential Ability Scales (DAS), Test of Early Mathematics Ability-3, Mental Rotation, or a combination thereof.

26. The method of claim 14 wherein the assessing the spatial cognitive ability of the subject demonstrates a deficit in the subject's spatial cognitive ability.

27. The method of claim 14 wherein the assessing the spatial cognitive ability of the subject demonstrates an enhancement in the subject's spatial cognitive ability.

28. The method of claim 14 wherein the subject has a disease.

29. The method of claim 28 wherein the reference pattern of manipulation behavior is data of one or more reference subjects administered an agent to treat or prevent a disease.

30. The method of claim 28 wherein the disease is a neurological disorder.

31. The method of claim 30 wherein the neurological disorder is selected from the group comprising Alzheimer's, a brain injury, or Parkinson's disease.

32. The method of claim 14 further comprising the step of administering a drug or a behavioral intervention designed to enhance spatial skills to the subject.

* * * * *